(12) United States Patent
Drucker

(10) Patent No.: US 9,572,530 B2
(45) Date of Patent: Feb. 21, 2017

(54) APPARATUS AND METHODS FOR IMAGING BLOOD VESSELS

(71) Applicant: QuickVein, Inc., Oakland, CA (US)

(72) Inventor: Steven H. Drucker, Oakland, CA (US)

(73) Assignee: QuickVein, Inc., Oakland, CA (US)

( * ) Notice: Subject to any disclaimer, the term of this patent is extended or adjusted under 35 U.S.C. 154(b) by 737 days.

(21) Appl. No.: 13/622,918

(22) Filed: Sep. 19, 2012

(65) Prior Publication Data

US 2013/0018254 A1 Jan. 17, 2013

Related U.S. Application Data

(63) Continuation of application No. PCT/US2011/029086, filed on Mar. 18, 2011.

(60) Provisional application No. 61/315,423, filed on Mar. 19, 2010.

(51) Int. Cl.
*A61B 5/00* (2006.01)

(52) U.S. Cl.
CPC ............. *A61B 5/489* (2013.01); *A61B 5/0077* (2013.01)

(58) Field of Classification Search
CPC ............................... A61B 5/0077; A61B 5/489
See application file for complete search history.

(56) References Cited

U.S. PATENT DOCUMENTS

| | | |
|---|---|---|
| 4,817,622 A | 4/1989 | Pennypacker et al. |
| 5,519,208 A | 5/1996 | Esparza et al. |
| 5,608,210 A | 3/1997 | Esparza et al. |
| 5,910,816 A | 6/1999 | Fontenot et al. |
| 5,947,906 A | 9/1999 | Dawson et al. |
| 5,969,754 A | 10/1999 | Zeman |
| 6,032,070 A | 2/2000 | Flock et al. |
| 6,178,340 B1 | 1/2001 | Svetliza |
| 6,230,046 B1 | 5/2001 | Crane et al. |
| 6,424,858 B1 | 7/2002 | Williams |
| 6,522,911 B1 | 2/2003 | Toida et al. |
| 6,556,858 B1 | 4/2003 | Zeman |
| 6,880,987 B2 | 4/2005 | Diana et al. |
| 6,889,075 B2 | 5/2005 | Marchitto et al. |
| 7,227,611 B2 | 6/2007 | Hull et al. |
| 7,239,909 B2 | 7/2007 | Zeman |
| 7,532,746 B2 | 5/2009 | Marcotte et al. |
| 7,904,138 B2 | 3/2011 | Goldman et al. |

(Continued)

FOREIGN PATENT DOCUMENTS

WO  WO 2011/116347  9/2011

*Primary Examiner* — Mark Remaly
(74) *Attorney, Agent, or Firm* — Levine Bagade Han LLP

(57) ABSTRACT

Various portable systems, devices and methods for imaging or visualizing blood vessels or other body tissue to facilitate accurate placement of a needle or other elongate instrument in blood vessels or other body tissue are described herein. In certain variations an imaging system for aiding needle insertion in a patient may include a mountable unit having an illumination source, an image sensor, and a display for displaying an image based on image information from the image sensor. The mountable unit may be configured for attachment to a hand of a user such that the user's hand on which the unit is mounted remains free to hold an object. The display may be positioned next to a needle insertion site during needle insertion by the user such that the needle insertion site and an image of the blood vessel and/or needle are simultaneously within the user's field of view.

16 Claims, 9 Drawing Sheets

(56) References Cited

U.S. PATENT DOCUMENTS

| | | |
|---|---|---|
| 2003/0004412 A1 | 1/2003 | Izatt et al. |
| 2004/0174444 A1* | 9/2004 | Ishii ............... H04N 5/232 |
| | | 348/240.1 |
| 2005/0168980 A1 | 8/2005 | Dryden et al. |
| 2006/0100523 A1 | 5/2006 | Ogle et al. |
| 2007/0161909 A1 | 7/2007 | Goldman et al. |
| 2009/0018414 A1 | 1/2009 | Toofan |
| 2009/0093761 A1 | 4/2009 | Sliwa et al. |
| 2009/0245601 A1 | 10/2009 | Cohen et al. |
| 2014/0276088 A1 | 2/2014 | Drucker |

* cited by examiner

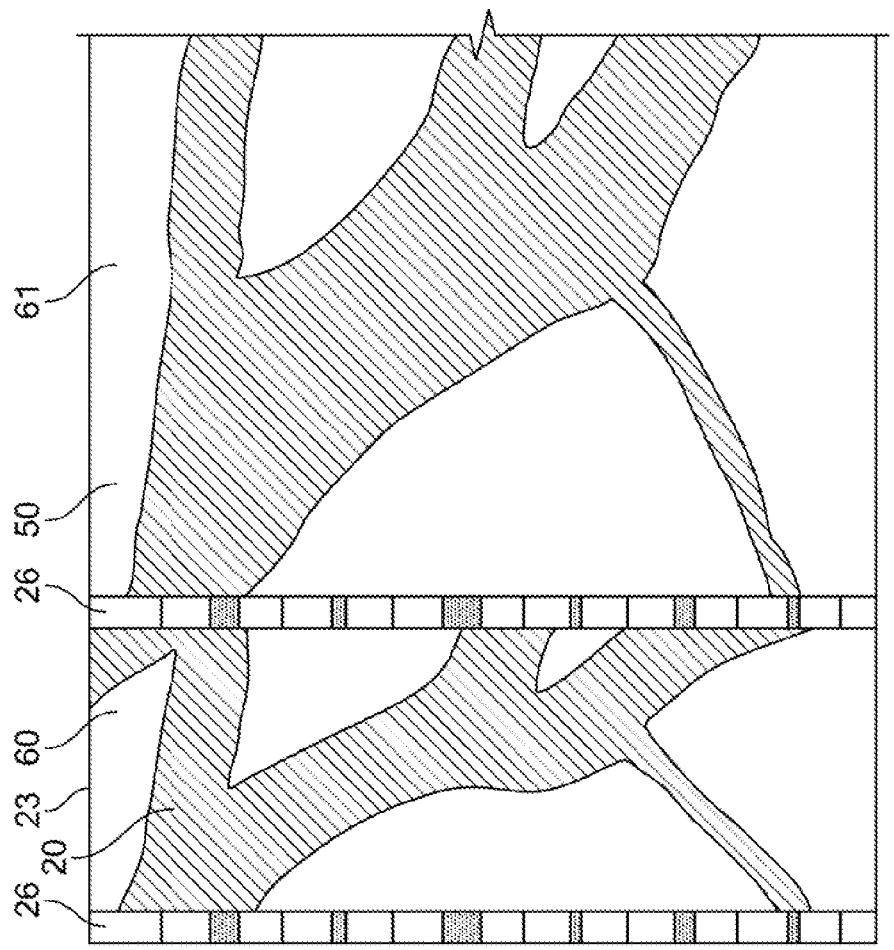
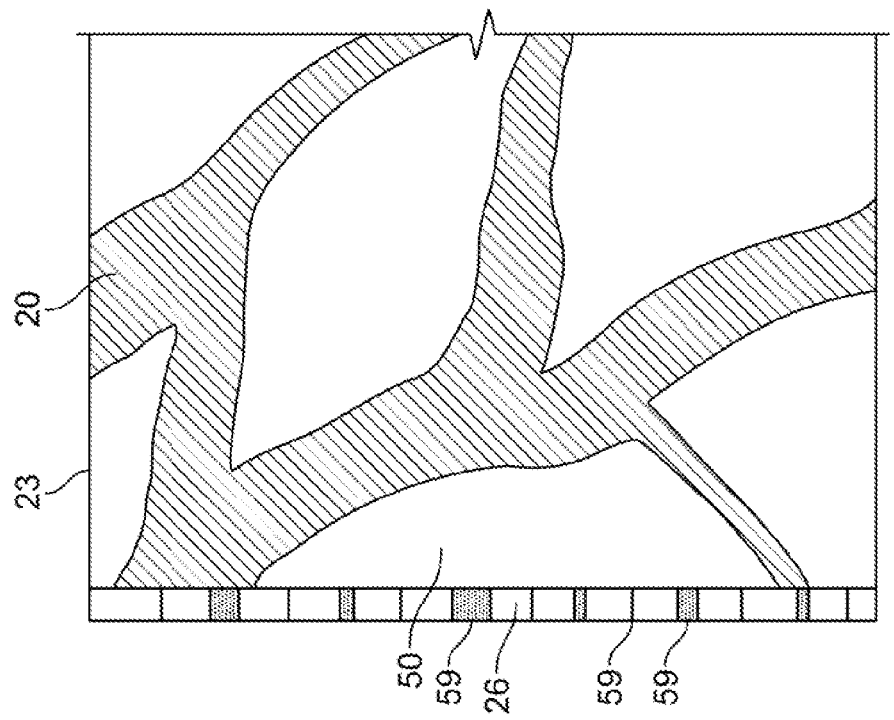

APPARATUS AND METHODS FOR IMAGING BLOOD VESSELS

CROSS-REFERENCE TO RELATED APPLICATIONS

This application is a continuation of PCT International Patent Application Number PCT/US2011/29086, filed Mar. 18, 2011, which claims benefit of priority to U.S. Provisional Patent Application Ser. No. 61/315,423 filed Mar. 19, 2010, the contents of each of which are incorporated herein by reference in their entirety for all purposes.

FIELD OF THE INVENTION

The present apparatus and methods relate generally to an improved portable system or device and method for imaging or visualizing blood vessels or other body tissue to facilitate accurate placement of a needle or other elongate instrument in blood vessels or other body tissue.

BACKGROUND

Inserting an intravenous line (IV) requires knowing where a suitable vein or other blood vessel is located and how large a needle the vein will support. For non-Caucasian individuals, females, small children and neonates, the elderly, obese individuals, those who have acute medical problems, and others, veins may not be visible. Individuals who exhibit more than one of the above traits often have veins that can be very difficult to find and may require multiple attempts to insert an IV.

In these difficult cases, caregivers have traditionally resulted to palpating the area around a potential vein site rather than locating a vein visually. When dealing with sick individuals, or when working in an area where spread of contagious diseases is likely, such as a hospital, this may not be possible. Blood pressure may be too low, or a vein may be buried too deeply to find by touch. Regulations designed to halt the spread of MRZA or other contagion may require the caregiver to wear gloves, severely diminishing touch sensitivity and the chances of finding a suitable vein. Problems with inserting a needle into a vein can result in escalation procedures which require additional personnel to become involved or a central line to be inserted by surgery adding to infection risk and compromising patient safety. In all cases, critical time and resources are wasted, patient discomfort is increased, and patient care is compromised.

Many of the existing vein viewers on the market use near IR illumination, a technique originally popularized by Eastman Kodak and published in "Medical Infrared Photography" (N-1), Eastman Kodak Company, 1969. The near IR radiation is transmitted and scattered by the skin and absorbed by the hemoglobin in the veins. Therefore, in near IR light, the area above a vein appears darker due to the hemoglobin absorption than the area around it.

When preparing to insert an IV, the user generally goes through two distinct phases, surveying the area to find a suitable site, and inserting the needle into the vein at the site. Existing vein viewers suffer from some or all of the following drawbacks: they require more than one person or more than two hands to operate the device and insert a needle in the patient; obstruct a user's view of a needle insertion site; have poor contrast and need dimmed light; require external device support to free a hand for IV insertion; and don't provide magnification. Some vein viewers require the user to change focus between viewing an image of an insertion site and actual insertion site; they don't remain stationary during needle insertion; and add mass to the needle insertion motion negatively impacting the ability to properly insert a needle. Some related patents include: U.S. Pat. Nos. 4,817,622; 5,519,208; 6,230,046; 6,032,070; and 7,904,138. Thus, there is a need for an improved blood vessel or body tissue imaging device and method that overcomes the drawbacks of existing vein viewers.

BRIEF SUMMARY

Various portable systems, devices and methods for imaging or visualizing blood vessels or other body tissue to facilitate accurate placement of a needle or other elongate instrument in blood vessels or other body tissue are described herein.

In certain variations an imaging system or device for aiding needle insertion in a patient may include a mountable unit having an illumination source, an image sensor, and a display for displaying an image based on image information from the image sensor. The mountable unit may be configured for attachment to a hand of a user such that the user's hand on which the unit is mounted remains free to hold a patient or a surgical instrument. The display may be mounted on or attached to the mountable unit such that the display and an image of a blood vessel and needle on the display are positioned next to a needle insertion site and the actual needle insertion site and the image of the blood vessel and needle are simultaneously within the user's field of view during needle insertion by the user.

Methods for imaging a blood vessel to aid needle insertion in a patient are provided. A variation may include scanning the patient with a hand mounted unit to locate a needle insertion site, the hand mounted unit having an illumination source, an image sensor, and a display for displaying an image based on image information from the image sensor. A patient may be held with a user's first hand on which the hand mounted unit is mounted or attached while the user's second hand holds a needle and the display and an image of a blood vessel and needle on the display are positioned next to the needle insertion site. Views of the actual needle insertion site and the display having an image of the blood vessel and needle thereon are provided to the user so that the user can view the actual needle insertion site and the image of the blood vessel and needle simultaneously while inserting the needle. The actual needle insertion site and the image of the blood vessel and needle may be viewed simultaneously by the user without changing focus.

BRIEF DESCRIPTION OF THE SEVERAL VIEWS OF THE DRAWINGS

FIGS. 10A-10C show representations of unmagnified and magnified views as seen on a display of a variation of an imaging system.

DETAILED DESCRIPTION

Figure 1A:
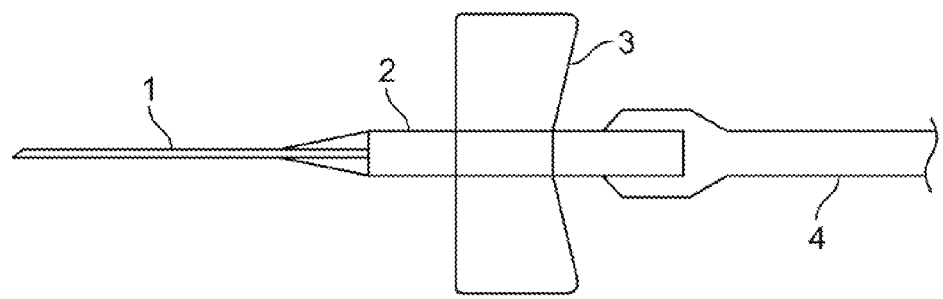
FIGS. 1A & 1B illustrate side views of typical IV insertion apparatus.
Figure 1B:
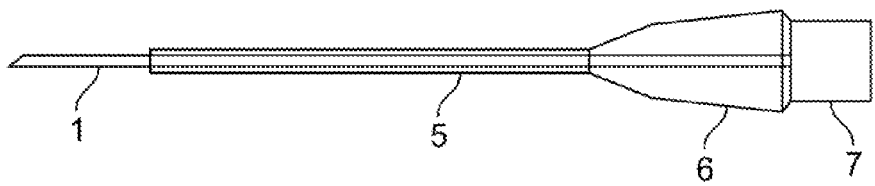

The systems and method described herein may provide imaging to aid in the insertion of various elongate instruments, such as needles, catheters, and micro-sensors in a patient. FIGS. 1A & 1B illustrate side views of examples of typical intravenous (IV) insertion apparatus.

FIG. 1A shows one example of a typical intravenous needle for small children which is commonly used for blood draws. The IV insertion apparatus may include a hypodermic needle (1) for piercing the patient's skin and vein. This needle may vary in length and/or diameter depending on the size of the patient and/or vein. For example, the needle for a neonate may have an exposed area of about 0.01 to 0.10 inches long or about 0.5 inches long and be about 0.10 to 1.0 mm or about 0.46 mm (0.018 inches) in outer diameter. A needle for an adult may be up to about 2 inches long and about 1.0 to 2.0 mm or about 1.65 min (0.066 inches) in outer diameter. The IV insertion apparatus may include, a transition tube (2) to which an optional gripping apparatus (3), e.g., a plastic wing may be attached. A tube (4) that connects to as blood collecting apparatus may also be provided. A Luer mount (not shown) may be used to connect the tube 4 to the blood collecting apparatus.

FIG. 1B shows one example of a typical intravenous needle apparatus for adults which is used for intravenous fluid insertion. The intravenous needle apparatus may include a hypodermic needle (1) or trocar for piercing the patient's skin and vein. Like the needle for blood draws described above, this needle comes in various lengths and diameters and is chosen on the basis of vein and/or patient size. The apparatus may include a cannula 5 which is a transparent plastic tube that fits over the needle and is inserted into the vein prior to needle removal. A Luer mount (6) that attaches to the catheter tube (not shown) and/or as needle termination (7) to aid in extracting the needle once the cannula is in place may be provided.

Figure 2:
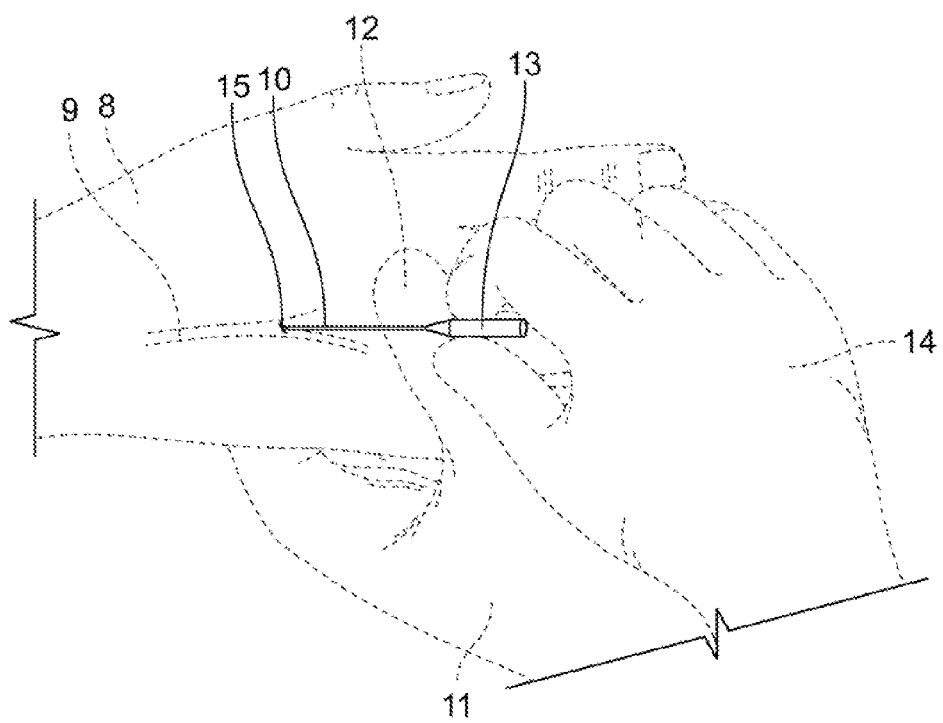
FIG. 2 illustrates a typical IV insertion.

As shown in FIG. 2, the typical procedure for inserting an IV needle involves the use of two hands. One hand (11) is used to hold the patient, in this case the patient's hand (8), at the insertion site. The thumb (12) of hand (11) is used to pin or apply pressure to a selected vein (9) and provide the proper needle insertion angle, e.g., about 20° to 30° from the plane of the insertion site (15). The second hand (14) is used to hold the needle (10) on or near the Liter mounting (13) and to insert the needle (10).

Various portable imaging or viewing systems, devices, tissue or vessel viewing apparatus and/or methods for aiding the insertion of an elongate instrument, e.g., a needle, in a patient into a blood vessel, artery, vein, capillary or other body tissue, are described herein. An imaging system or device may be mountable or attachable to a hand (e.g., finger, thumb, metacarpus and/or wrist). In certain variations, the imaging system may optionally be mounted or attached to an arm, elongate instrument or needle inserter. The imaging system or device may be in the form of a mountable unit having an illumination source, an image sensor or image detector, and/or a display. The display may display an image based on image information received from the imaging sensor, e.g., an image of a blood vessel and/or needle.

The mountable unit may be attachable to a user's hand in a manner that allows the user's hand on which the unit is mounted or attached or affixed to remain free for use, e.g., free to hold or grasp a patient or a surgical instrument. The display may be mounted on or attached to the hand mountable unit so that the display and an image of a blood vessel and/or needle shown on the display are positioned net to a needle insertion site on a patient while the user is inserting a needle into the patient. The positioning of the display next to the needle insertion site allows the actual needle insertion site and the image of the blood vessel and/or needle to remain simultaneously within the user's field of view during needle insertion by the user. The positioning of the display next to the needle insertion site may provide the user with a side by side view of the actual needle insertion site and the display having an image of the blood vessel and/or needle allowing the user to view the actual needle insertion site and the image of the blood vessel and/or needle simultaneously without changing focus or refocusing while inserting the needle.

The imaging systems and devices described herein may be separate units, (e.g., separate from a needle) mounted or attached to the hand of the caregiver used to hold a patient. As a result, the device remains stationary during needle insertion by the caregiver, the needle being inserted by the caregiver's other hand and the device not coupled or mounted on the needle. The devices don't add mass to the needle insertion motion or to the needle, allowing for easy manipulation and avoiding disruption of or impacting the ability to properly insert a needle, such as an IV needle. The imaging systems and devices in use provide a view of the actual needle insertion site is in its natural state, unobstructed by a projection or projected image. There is no fatigue to the eyes that often results from the projection of laser light. The device, system or mountable unit may be configured in size and weight to allow for easy manipulation with one hand and so as not to interfere with normal needle insertion motion or hand use when the device is attached.

Figure 3A:
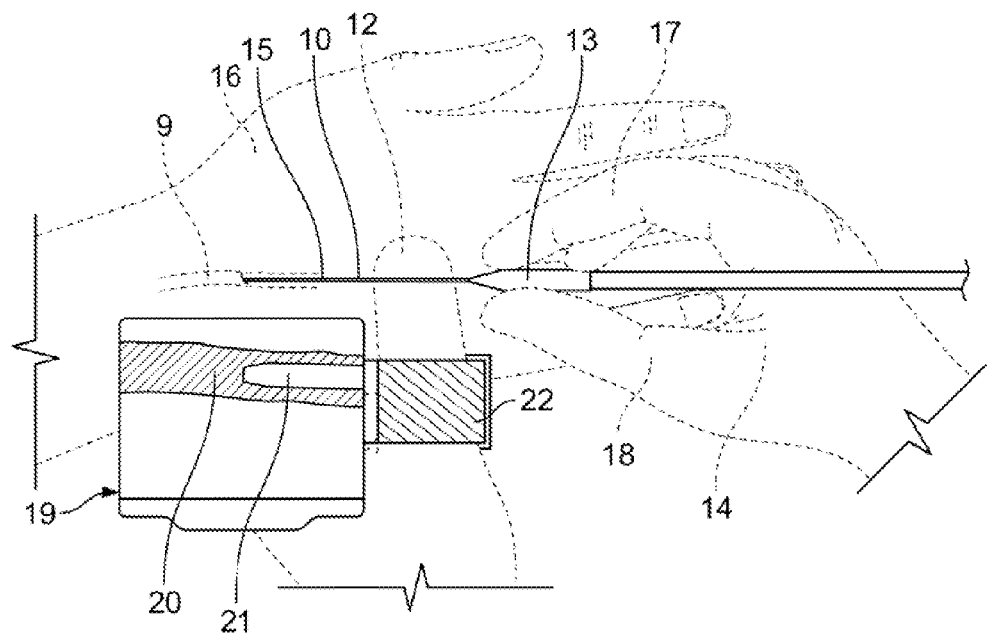
FIG. 3A illustrates a variation of an imaging system in use during an IV insertion procedure.

FIG. 3A illustrates a variation of an imaging system 19 in use during an IV insertion procedure. Imaging system (19) is attached to the stationary (gloved or ungloved) thumb (12) that holds the blood vessel e.g., a vein. The imaging system (19) may partially rest on the patient's skin or the caregiver's hand as the caregiver holds the patient with the thumb 12 on which the imaging system 19 is attached. Alternatively, the forefinger (17), thumb (18) or the hand used to insert the needle may serve as attachment sites for the imaging system 19. The imaging system (19) may include an attachment component (22), e.g., Velcro, an elastic strip, a strap, a latch or other suitable attachment mechanism, for securing the imaging system (19) to the caregiver, such that imaging system (19) may be placed appropriately near, next to, or adjacent the insertion site, vein and/or needle during needle insertion by the caregiver.

While using the imaging system (19) to aid needle insertion, the caregiver's line of site to the needle at the insertion point remains unobstructed as the line of site is behind and in line with hand 14. The imaging system (19) does not require additional support structures, and use of the imaging system (19) mounted on the caregivers hand does not interfere with standard needle insertion methodology or current needle insertion practice. Indeed, one hand of a caregiver can hold the needle for insertion and the other hand of the caregiver (or a portion or protuberance of the imaging system (19) mounted thereon) can hold or press on the vein. Imaging, system (19) takes seconds to setup and secure to the attachment point on a caregiver. In certain variations, the imaging system (19) may show a magnified view of the needle (21) and the vein (20) adjacent to and/or on a similar plane to that of the actual needle insertion point, allowing the caregiver to see both the needle and insertion site without having to refocus. Optionally, the front edge of the imaging system (19) may be designed to partially rest on the patient's skin, e.g., on the patient's arm (16). The imaging system (19) is also designed in such a way that it can be cleaned and disinfected using an alcohol rub or other sterilizing solution.

Figure 3B:
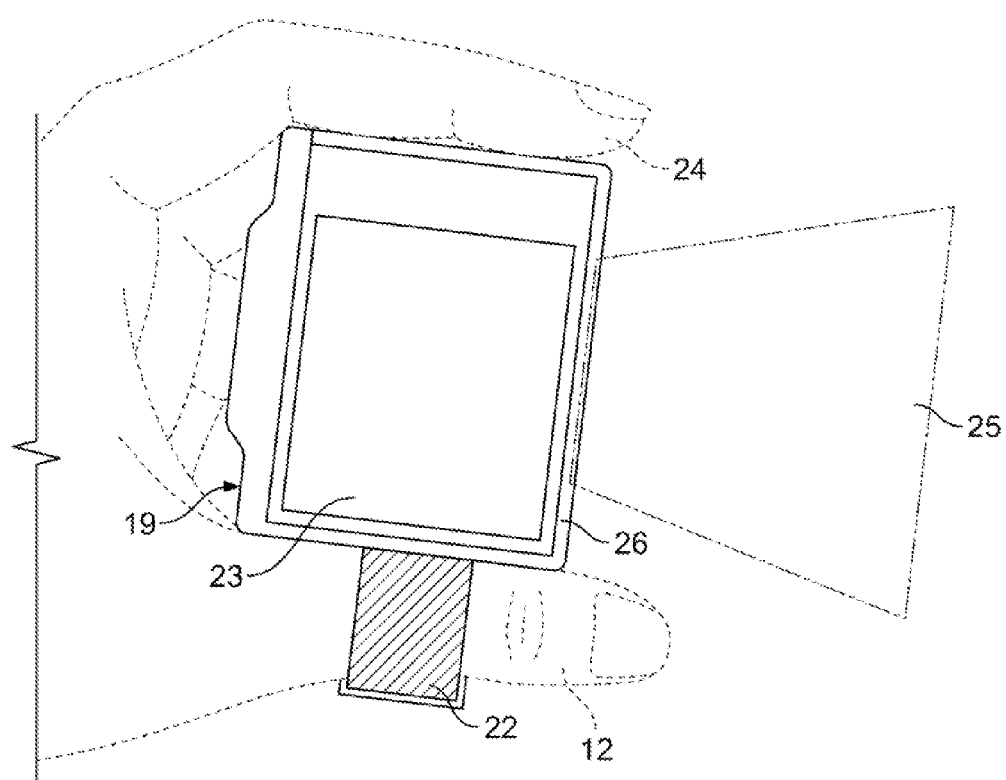
FIG. 3B illustrates at variation of an imaging system in survey mode.

FIG. 3B shows a variation of an imaging system (19) in survey mode. The imaging system (19) may be attached to the caregiver's thumb (12) while optionally being held or supported by the forefinger (24). In certain variations, the imaging system (19) could attach directly to the caregiver's hand, or alternatively to the caregiver's hand and/or fingers only. The caregiver can survey the patient's vascular system by moving their band with attached imaging system (19) over the patient's body. The area being surveyed is shown within the dashed lines (25). The blood vessel images will appear on the display (23). The full field of view, demagnified as necessary, may be shown on the display. The edge of the base-plate (26) or other portion of the imaging system (19) may be visible in the image on the display and serve as a reference point for the location or alignment of the imaged blood vessel relative to the patient's body or the imaging system (19).

In certain variations, the imagine system (19) may provide numeric information on the size of a blood vessel closest, to the imaging system (19) edge using algorithms based upon contrast gradations in the blood vessel's cross-section. The imaging system (19) may also include a mechanism for increasing or decreasing magnification of the image.

Figure 3C:
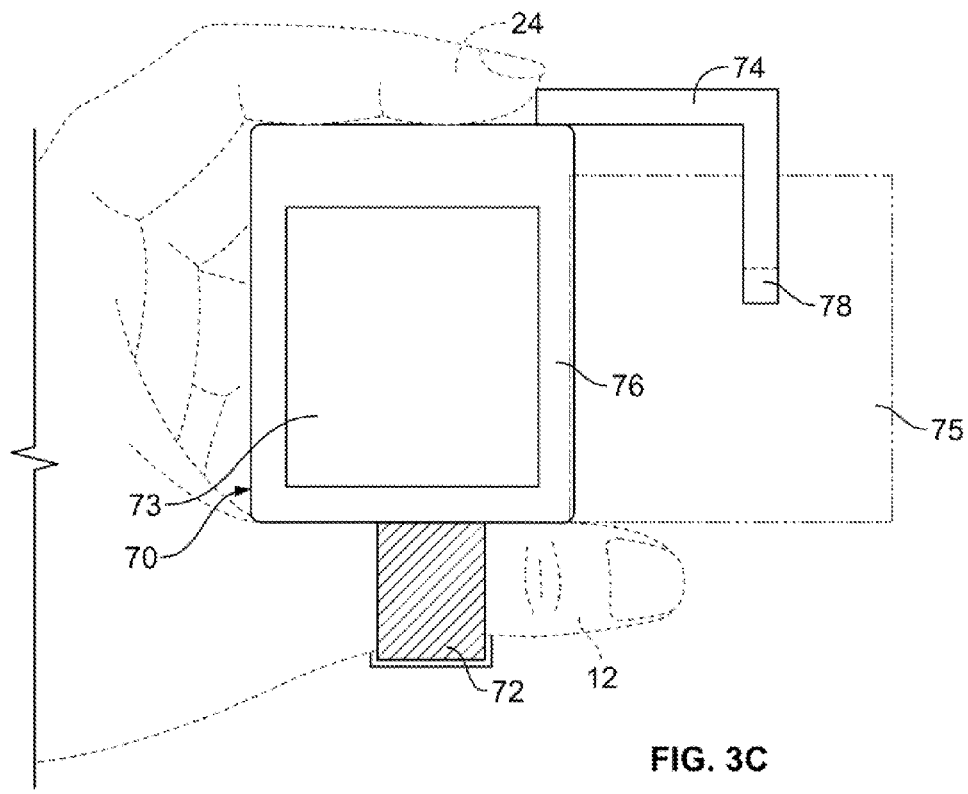
FIG. 3C illustrates a variation of an imaging system.

FIG. 3C shows a variation of an imaging system 70 having a stalk 74 with a camera 78 positioned thereon. The system 70 includes a display 73 and an attachment component 72 and base plate edge 76. The system 70 provides a rectangular survey area 75.

Figure 6:
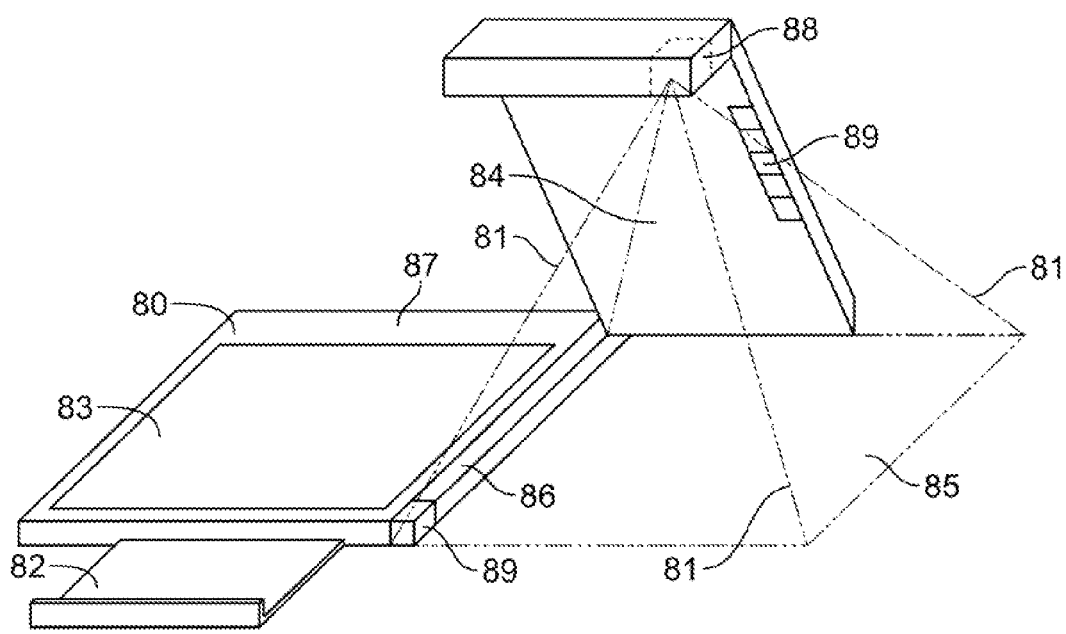
FIG. 6 illustrates another variation of an imaging system.

FIG. 3B shows a variation of an imaging system providing a survey area 25 that is trapezoidal in shape. The processor of the imaging system may present a trapezoidal view or image on the display or alternatively may truncate the survey area. In other variations, as shown in FIG. 3C or 6, the imaging system provides a survey area that is rectangular and closely matches the aspect ratio of the display.

Figure 4:
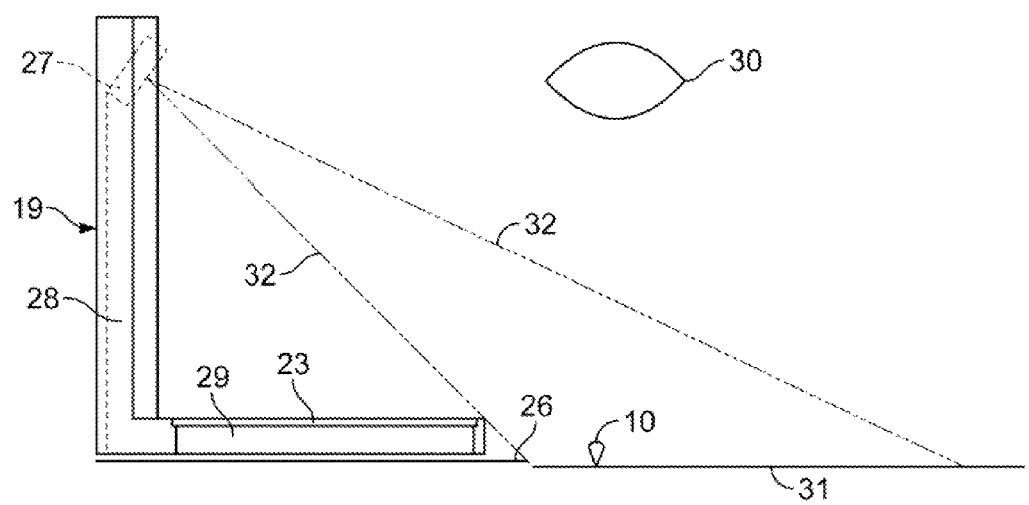
FIG. 4 illustrates a light path and line of sight of one variation of an imaging system.

FIG. 4 shows a side view of imaging system (19) positioned an or near the patient's skin 31. The imaging system (19) includes an electro-optical module (27) which has an image sensor, e.g., a camera or other image detector, and may contain the illumination source. The camera line of sight lies between the dashed lines (32) and includes the edge of the base-plate (26). An electronics module (28), which includes the processor and a voltage generator, is situated way from the patient's skin. The battery (29) for powering the imaging system is located beneath the display (23). The caregiver's eye (30) may be located anywhere from 4 inches to 30 inches away from the imaging system (19) and may be situated above the imaging system. The caregiver's eye may be located at a distance comfortable for the caregiver to view the display (23) and patient's skin (31). The caregiver has an unobstructed view of both the display image and the patient's skin or actual insertion site, and depending on the eye to skin distance is able to see both without changing focus.

In one variation, the optics line of site (32) may be arranged so that the camera and illumination source are at an angle to the skin rather than perpendicular to the skin. As a result, most of the specular reflection from the skin's surface is reflected away from the camera-optics subsystem and does not degrade the image quality. The needle (10) may be imaged by a thin line of specular reflection, however, most of the light from the illumination source is specularly reflected away from the camera due to the round shape of the needle.

Figure 5:
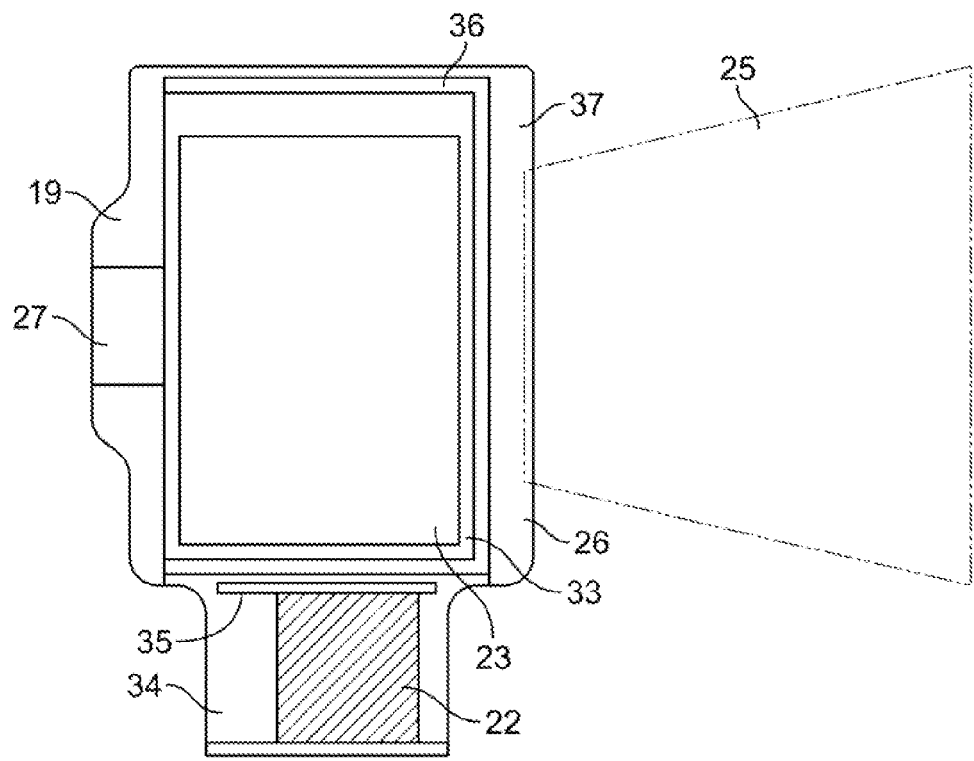
FIG. 5 illustrates a top view of a variation of an imaging system.

FIG. 5 shows another variation of imaging system 19. The area being imaged by the camera (27) is shown within the dashed lines (25), which is a trapezoidal area. The imaging system includes a display (23) within a display module (36). A base plate (37), which may be removable or rotatable to accommodate left or right handed users of the system may underlie display module (36). As described before, the edge of the base plate (26) is present in the image to provide a reference point to the system user. A base plate thumb rest (34), along with the thumb attachment strip (22) and attachment strip holder (35) are also provided.

FIG. 6 shows another variation of an imaging system 80. The imaging system 80 includes a display (83), a thumb rest (82), and a base plate having a base plate edge (86). An electronics module (84) and an imaging sensor, e.g., a miniature camera (88) are located at a far end of the imaging system 80, adjacent to the display module 87. The camera (88) is positioned above the survey area (85). The dashed lines (81) show the field of view of the camera, which provides a rectangular view of the patient's skin and the blood vessels positioned therein, e.g., veins. The rectangular view of the patient's skin provided by the camera 88 may have an aspect ratio that matches the aspect ratio of the display (83). The camera 88 may have a line of sight that may be substantially perpendicular to the plane of the patient's skin.

The imaging system 80 may also include a light or illumination source (89). The illumination source 89 may be positioned at an angle relative to the image sensor, e.g., camera (88), so that specular light is reflected away from the camera 88, helping to improve image contrast. The illumination source 89 may be mounted on the electronic module (84) such that it directly illuminates the survey area (85). Optionally, the illumination source 89 may be mounted on the display module (87) to provide a beam of light that bounces off the electronics module (84) and on to the survey area (85).

Due to the angle a needle is positioned relative to the skin during needle insertion, the optical path to the needle is at a more acute angle than the optical path to the skin. Typically, a needle includes a polished metal, e.g., stainless steel, and displays a high degree of specular reflection. Depending upon the location of the illumination source radiation impinging on the needle, the radiation impinging on the needle may be reflected away from the optics. In certain variations, the needle itself is not imaged, but instead, the needle's shadow is imaged since the needle blocks radiation reflected from the tissue underneath the needle.

Figure 7A:
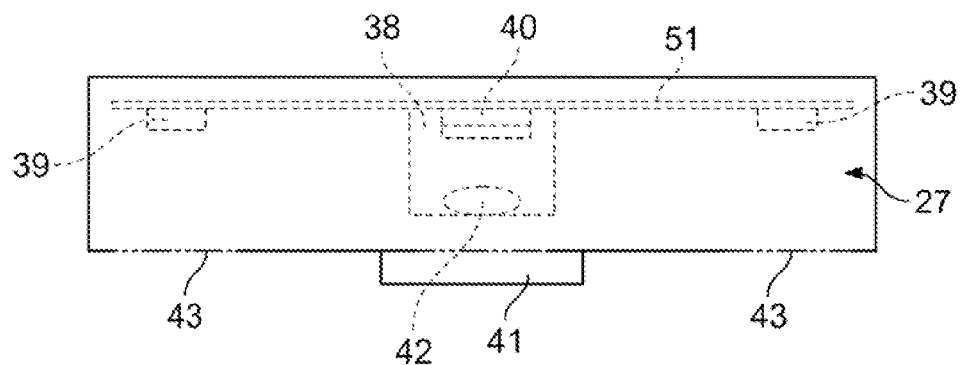
FIG. 7A illustrates an electro-optical module of a variation of an imaging system.

FIG. 7A shows one variation of an electro-optical module (27) of an imaging system having various electro-optical elements. The electro-optical module (27) may include one or more illumination sources (39), a clear aperture (43) through which the illumination source 39 projects light onto the skin, a camera module 38 having one or more sensors (40), e.g., video sensors, and/or one or more lenses (42), and/or an IR pass filter (41) or other illumination or light source filter and circuit board 51. The electro-optical module (27) and electro-optical elements may be coupled or connected to the rest of the imaging system using as PC board (42) and cable or a flexible PC board. The camera may be positioned substantially at an angle relative to the skin horizontal, which produces a trapezoidal field of view.

Figure 7B:
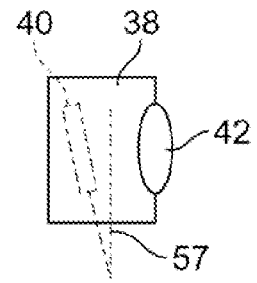
FIG. 7B illustrates a side view of an electro-optical module of a variation of an imaging system including a sensor canted with respect to a lens.

FIG. 7B shows a close-up of a variation of camera module (38). In this variation, the sensor (40) is canted or titled at an angle (57) with respect to the lens (42). Canting the sensor 40 with respect to the lens 42 or the lens 42 with respect to the sensor 40 can correct for a trapezoidal shaped viewing area, making it rectangular.

Figure 7C:
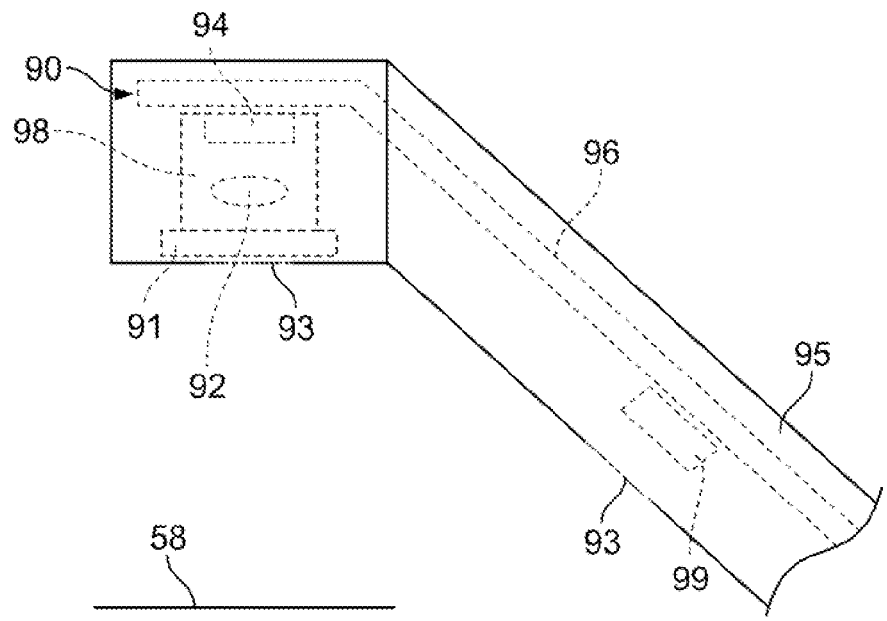
FIG. 7C illustrates an electro-optical module of a variation of an imaging system.

FIG. 7C shows a variation of an electro-optical module (90) having a camera positioned substantially perpendicular to the skin horizontal. In one variation, a camera is mounted on a camera module 98 and an illumination source 99 is mounted on an illumination source holder stalk 95. The stalk (95) may be attached or coupled to a combined electronics or display module (not shown) in a variety of configurations, e.g., in a manner similar to how the electronics module (28) is attached to the display module in the imaging system shown in FIG. 6. The camera line of sight may be substantially perpendicular to the plane of the patient's skin (58). The electro optical module includes an IR pass filter 91, sensor 94, lens 92, clear aperture 93, and circuit board 96.

Figure 7D:
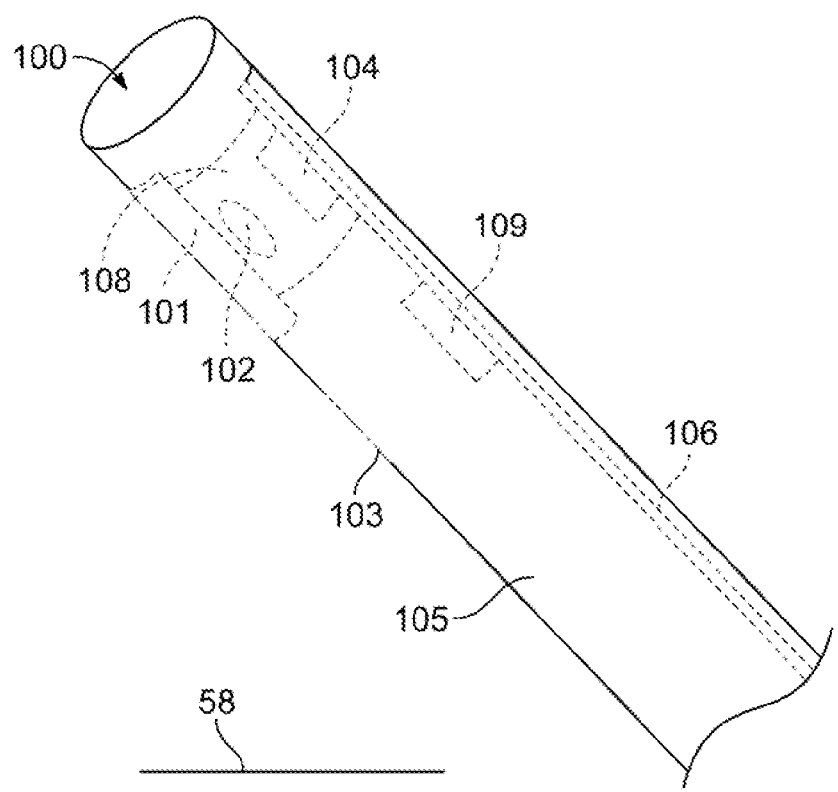
FIG. 7D illustrates an electro-optical module of a variation of an imaging system.

FIG. 7D shows another variation of an electro-optical module (100) having a camera module (108) and illumination source (109) mounted in a round or rectangular camera stalk (105). The camera module (108) and illumination source (109) are both positioned at an angle to the field of view and the approximate plane of the patient's skin (58). The lens (102) is canted with respect to the sensor (104) to correct the aspect ratio of the field of view. Canting of the lens (102) with respect to the sensor (104) is one alternative to correcting the field of view. Optionally, a processor within the imaging system may correct the field of view. The electro optical module includes an IR pass filter 101, aperture 103, and circuit board 106.

A variation of an imaging system may include one or more of the following components: An optical filter or light or IR filter (41), which may be positioned in front of a camera module (38). An IR filter blocks visible light, while passing IR radiation. Hemoglobin absorbs IR radiation from 700 nm and higher, and all skin types are transparent above 750 nm, thus IR radiation may be used to image a blood vessel or other tissue having hemoglobin therein. Various filters may be used for filtering or blocking reflected light. Reflected light may be detected off of the skin to obtain an image.

An optics sub-assembly may be provided. The optics sub-assembly may have at least a 30° field of view and may be capable of focusing in a range of about 1 inch to 5 inches or more. The optics sub-assembly may include a lens. The optics sub-assembly may be self-focusing or may include an aperture stop to provide the necessary depth of view. In certain variations, the resolution required to view an object may be about 10 times the size of the smallest element to be resolved. For example, a neonate having a vein that is about 1 mm in diameter or 0.04 inches would require a resolution of 0.004 inches when using a 12 ram needle with 0.45 mm diameter. In another example, an adult having a vein that is equal to or greater than 3 mm or 0.12 inches in diameter uses a 40 mm long needle of 1.1 mm diameter and would requires a an optical resolution equal or better than 0.012 inches.

A two dimensional image sensor, e.g., a video sensor camera 40, having a variety of resolutions may be provided. For example, a video sensor camera may have about 680 horizontal by 480 vertical pixels, but other lower and higher resolution cameras may optionally be used.

When using a variation of an imaging system as described, herein for aiding in the insertion of an IV in a patient, an optimum distance from the skin to the optics may be between about 2 inches and about 6 inches or greater depending on lens. At this distance and depending on the field of view of the camera, the width of the picture or image is roughly equal to the distance between the optics assembly and the skin, so at 2 inches the horizontal resolution of a camera pixel is approximately 0.002 inches and at 6 inches the horizontal resolution of a camera pixel about 0.006 inches. This provides sufficient information to resolve a vein of 1 to 5 mm diameters. The vertical resolution may be lower but may still be more than sufficient for viewing.

The sensor signal-to-noise ratio (S/N) may also be an important consideration. Light scattering from internal surfaces within the skin diminishes the difference in contrast between a vein and the surrounding area. The better the S/N, the more dynamic resolution the system will have and the system will be better at discriminating between vein and non vein areas and displaying deeper veins. In certain variations, the image sensor or video sensor may have variable gamma correction to tailor the dynamic range of the image sensor camera to more fully resolve small skin contrast differences. This feature is helpful in when viewing deeper veins where significant scattering of light from the intervening tissue back to the image sensor or camera occurs.

An illumination source may be provided. In certain variations, the illumination source may be in the form of one or more IR LEDs having wavelengths within a hemoglobin absorption band and where substantial interference from water absorption bands is not present. The location of the illumination source may depend upon the optical path. The location of the illumination source may be arranged with respect to the camera module such that the light generated in the illumination source does not couple directly back into the lens-sensor system and/or to minimize specular reflection back to the camera subsystem.

An illumination or IR source may be positioned in an electro-optical module (as shown in FIGS. 6-7C), separate from such a module or at another position on an imaging system. In certain variations, the number of LEDs used to illuminate the skin may be selected based on illumination intensity and camera sensitivity to maximize signal-to noise ratio and minimize power consumed. In certain variations. IR sources may be pulsed synchronously with the frame rate of a camera with the camera electronic shutter open during the illumination period and closed at other times to decrease the effect of specular reflection from other stray sources and potentially reduce power consumption further.

Figure 8:
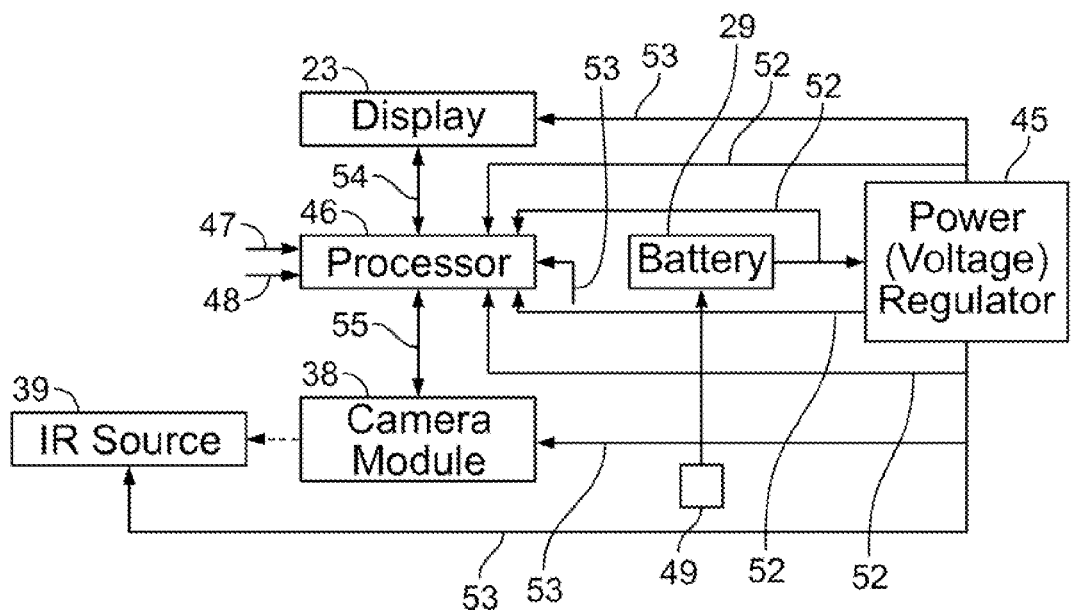
FIG. 8 illustrates an electronic block diagram of a variation of an imaging system.

FIG. 8 shows the corresponding electronic block diagram for a variation of an imaging system. The system includes an electro-optical module (27), a display (23), a battery (29) for power, a processor (46), voltage generation or regulator (45) supplying power (53) to the various modules, illumination source (39), miscellaneous input devices for user control

(47) and (48) such as, e.g., manual magnification, On-Off, and external power input plug (49) for recharging the battery. A scanned image may be passed from the camera module (38) to the processor (46) which outputs an enhanced image to the display (23) showing the targeted body tissue, e.g., veins or other blood vessels beneath the skin.

The processor (46) may have one or more of the following functions: It controls the image sensor and gets image data (54); Provides contrast enhancement to make blood vessels more visible; Magnifies or demagnifies the image as required; Selects the region of interest for display during insertion based upon needle position; Adds false color to the image to highlight information; Provides information as to blood vessel depth; Provides information as to blood vessel diameter; Corrects or compensates for image distortion where the angle of the image sensor would normally present a trapezoidal viewing area; Sharpens the blood vessel edges in an image; Rotates the image as appropriate to match the user's perspective; Provides a different magnification or alters the magnification if a needle is detected in the image; Uses the display to show the degree of image magnification; Monitors user inputs; Controls and monitors power (52); and/or Outputs the image and/or data for display (55).

In certain variations, a camera may control (56) the illumination source(s) based upon input from the processor. A rechargeable battery may be utilized to provide power for the system during operation. The display may show a view or image of a blood vessel, e.g., a vein, either while scanning or surveying the patient for suitable needle insertion or IV sites or when preparing to insert a needle.

Figure 9A:
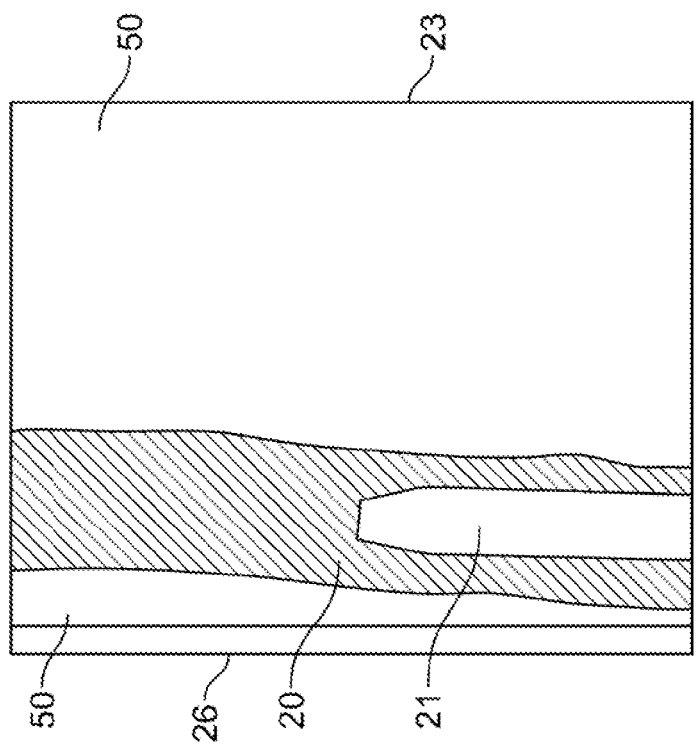
FIG. 9A is a representation of an unmagnified image of a blood vessel as seen on a display of a variation of an imaging system.

FIG. 9A is a representation of an unmagnified view or image of a blood vessel as seen on a display 23 (via an image sensor or camera) of a variation of an imaging system described herein. There is DO needle present in the image. The full field of view as recorded by the image sensor or camera is displayed on the display 23. This view may be use fill in surveying a patient to find a suitable spot to insert a needle. Once a suitable spot is located, the caregiver may mark the spot for needle insertion, e.g., with a marking apparatus or by pressing a finger against the spot.

In certain variations an imaging, system may include features for providing magnification. For example, magnification may be enhanced or reduced by pressing, or activating a switch, rotating a thumb wheel, or tapping or touching the display on the system, which would allow a user to cycle through various magnifications available and to cycle back to the original representation or magnification if desired. A magnified image may replace a non-magnified image or both may be present in a visualization display. Magnification of the insertion site may take place without having to change the position of the imaging system or device and without affecting access or view of the vein. In certain variations, a processor of the imaging system may be used to add color to the blood vessels and/or sharpen the edges of the blood vessels to provide additional information or detail regarding the insertion area or blood vessels to assist the caregiver in blood vessel selection. The display may show blood vessels, e.g., Veins (20) beneath the skin surface, the edge of the display, display module, back-plate (26) or other portion of the imaging system or mountable unit and/or the part of the body in view (50).

Figure 9B:
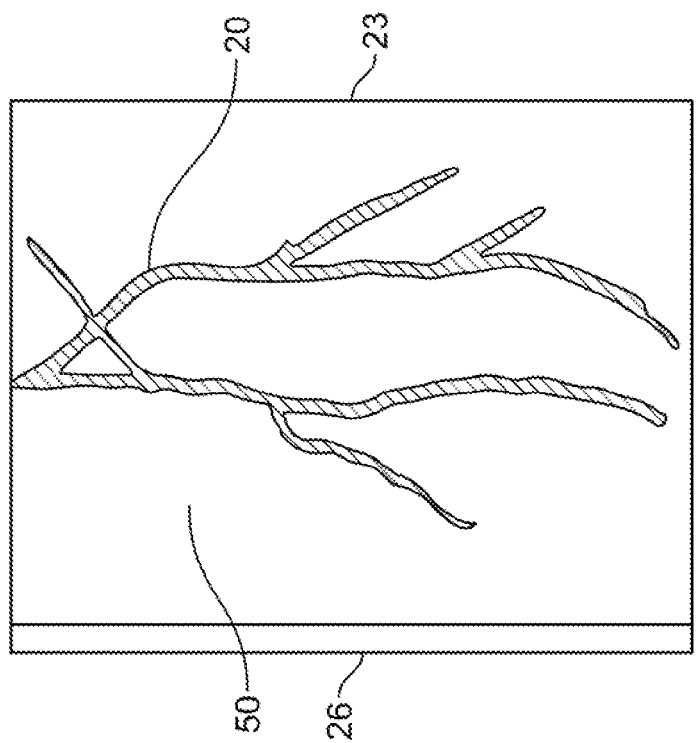
FIG. 9B is a representation of a magnified image of a blood vessel and needle as seen on a display of a variation of an imaging system.

FIG. 9B shows a representation of a magnified view or image of a blood vessel and needle as seen on a display (via an image sensor or camera) of a variation of a blood vessel imaging system. The view shows the patient's skin (50), blood vessel, e.g., vein (20), and the shadow of the needle or the needle (21). The magnification of the view may be automatically selected based upon the width, in pixels, of the needle. The smaller the diameter of the needle, the larger the magnification.

In one example, a variation of an imaging device as described herein is used to aid in needle insertion in a neonate whose largest peripheral vein is about 1 mm or 0.040 inches in diameter. A needle that is about 0.018 inches in diameter is used and a caregiver should insert a needle at the center of the vein (within about 0.006 inches) to prevent or minimize vein movement. The processor of the imaging system would display an image of the area around the tip of the needle magnified by a factor of 4 to 16 to aid or facilitate accurate needle placement or insertion in the vein.

In another example involving needle insertion in an adult, with the caregiver using a needle of diameter 1.46 mm, 0.066 inch, the processor of an imaging device would select a magnification between 2 and 4. This magnified view is useful in allowing the caregiver to precisely determine the center of a vein and to properly align the needle to the direction of the vein.

Optionally, the processor may color the black shadow of the needle or the needle in the image on the display to make it clear that it is the needle. Optionally, the processor may color the blood vessels and/or sharpen the edges of the blood vessels to provide additional information or detail to the caregiver to make preferred or optimal needle placement more apparent or obvious to the caregiver.

In certain variations, the imaging system or mountable unit may include a detachable or rotatable base plate. Different base plates may be used or attached for different usages. A base plate allow for the attachment or mounting of the imaging system to the outside of an IV Insertion Luer fitting. A base plate may include a bottom strap for attaching the imaging system to the hand or fingers. Optionally, a detachable base-plate, may be re-attached after rotation by 180 degrees to permit a care-giver to use a different hand, either the right or left hand.

In certain variations, a display may include a lid or cover that protects the display, e.g., when the display is being carried from place to place. The lid or cover may snap, slide, or roll onto or off the display, to expose or protect the display in another variation, a lid, or cover may attach to a base-plate and fold over the display.

In certain variations, electronics or working components of the imaging system may be packaged in a display module. The image sensor, e.g., a camera, may be attached to the display module with a camera stand or stalk (44) (e.g., as shown in FIGS. 7C-7D). In certain variations, a camera stand or stalk (44) may plug or connect into either side of the display-electronics module. This allows for right or left handed operation or permits replacing the camera if it gets damaged no longer functions. Optionally, the camera stand or stalk (44) may slide or collapse into and out of the display-electronics module for easy stowing and protection while traveling.

In certain variations, a magnified view or image of a blood vessel and a portion of a needle may occupy pan of a display while a non-magnified view of the blood vessel occupies the rest of the display. Thus, magnified and unmagnified images of a blood vessel or insertion site may be provided simultaneously on a single display. In certain variations, a magnified image may be inserted into the non-magnified image where the magnified image insertion point is near the actual end of the needle so the caregiver or imaging device users field of view covers both.

A variety of magnification features may be provided in the imaging systems described herein. FIG. 10A shows an enlarged version of a vein image whose size on the LCD display would be 1:1 with respect to the original.

FIG. 10B shows a 1:1 vein image 60 (where magnification is 1:1 in both horizontal and vertical directions) which may cover ⅓ of the display 23 area while the remaining area of the display 23 shows an image 61 of veins 20 that are magnified in the horizontal direction at 2:1 magnification with the vertical direction remaining at the 1:1 magnification. Proportion of magnified to non-magnified images on a display may vary or change. A 4:1 or 8:1 magnification of a vein, depending on the vein's size, may require more screen space to see the whole width of the vein than a magnification of 2:1 would. The magnifications may vary (greater magnification or less magnification) as selected by the operator or user of the imaging system. A magnified view may occupy one portion of a display and non-magnified image can occupy another portion of the display. Optionally, a magnified image may be inserted into the non-magnified image where the picture insertion point is near the actual end of a needle so a caregiver's field of view would cover both.

Figure 10C:
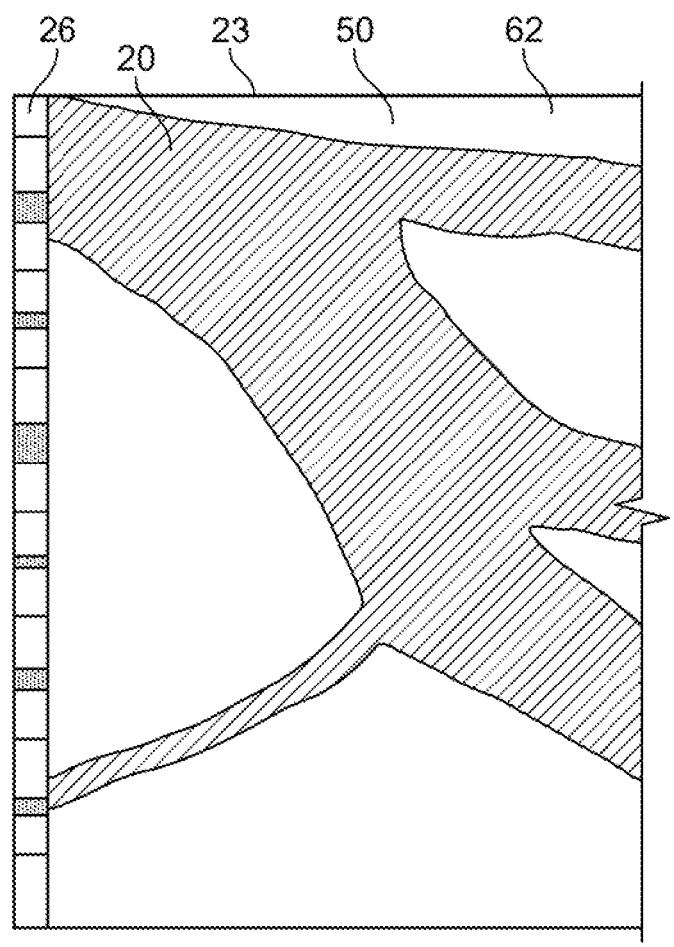

FIG. 10C shows a display 23 with an image 62 of veins 20 having 1:1 vertical magnification and 2:1 horizontal magnification.

The displays 23 used to display the images in FIGS. 10A-10C may also include markings 59 on a reference scale located on an edge 26 of the display. The markings 59 on the reference scale on the edge 26 of the display 23 are captured by the image sensor and are shown in the image on the display 23 to show the imaging system user the alignment of the image relative to the patient's body.

In use, any of the imaging systems or devices described, herein may be used to provide an image of a blood vessel to aid needle insertion in a patient in one variation, a caregiver may scan or survey a patient with a hand mounted imaging device to locate a needle insertion site. The caregiver's first hand, on which the imaging system is mounted, holds the patient as the display of the imaging, system and an image of a blood vessel and needle on the display is positioned next to the needle insertion site. Various views or a side by side view of the actual needle insertion site and the display having, an image of the blood vessel and/or needle thereon allow the caregiver to view the actual needle insertion site and the image of the blood vessel and/or needle simultaneously while holding and inserting the needle with the caregiver's second hand. The actual needle insertion site and the image of the blood vessel and/or needle may be viewed simultaneously by the caregiver without requiring the caregiver's eyes to change locus.

A display may include or depict the visual representation of the output of an electronic device. Examples include but are not limited to LCD, OLED, Pixel Qi, Mirasol, elnk, DLP, Plasma, and/or CRT or other display or image viewing apparatus or devices that can be manipulated, portable, or adjustable. A display may be wireless or directly connected. Examples, include smartphones or other mobile devices.

Examples, of attachment mechanisms for attaching the imaging system or device or mountable unit to the hand, thumb, finger, wrist, arm, etc., include but are not limited to Velcro, elastic bands, clamps, latches, and/or slides, such as movable locking slides. One requirement is the ability to clean and disinfect or replace the mechanism easily to prevent disease transfer and allow for removal of blood. A latching slide that lets the user adjust the opening and hold pressure and can be readily wiped down may be used.

In certain variations, a sensitive CMOS camera, IR LEDs, IR filter, and/or processor may be utilized to produce an image which enhances blood vessel or vein contrast. The LEDs may be used to illuminate the skin area. Reflected light may be passed through an IR filter and is imaged on the camera or image sensor. The camera's output signal is fed to the processor which enhances the vein contrast and formats the picture for the display.

The imaging systems or devices described herein provide great performance in a small, ergonomic footprint. The following devices or components may be utilized in the imagine systems and devices described herein: small, inexpensive, high brightness, color graphics, low current LCDs; small, high resolution wafer scale lens that has the volume of ⅛ of an eraser head; Low power, high sensitivity, large gray scale CMOS or CCD single chip integrated, camera; high speed digital signal processors with under 100 mw power dissipation; high density Li Ion battery; and/or other small LCDs and processor technology that can be used to create the portable hand mounted imaging systems and devices described herein.

The image provided by an imaging system or device may be referenced to the position of the users hand or arm and may not be affected by the orientation of the user's head. The user can look around as necessary while the image remains on the display, next to the actual insertion site. In use, the imaging system or device is attached or mounted or passively mounted to a hand such that it follows the movement of the hand. An image may be viewable along an axis of the hand or thumb may be provided. By using the imagine systems or devices as described herein, the user is provided with it virtual and as real image of the insertion site at the same time. The imaging systems or devices described herein may be attached to a hand or thumb in a manner that allows the thumb to remain available, and able to perform opposing motion to hold or grab an object. A user's band may hold at patient, while a portion of the attached imaging device or system lies on the user's hand.

An imaging system or device described herein may achieve the following: have the ability to magnify an image so veins and needle placement on neonates and small children is readily visible; clearly show the position of the vein relative to the needle, regardless of vein and needle diameter; operate in ordinary illumination, remain positioned close enough to the point of IV insertion so that the user can easily see the insertion point and magnified image; does not obscure site visibility, is easily portable and easy to move to different areas on a patient's body; and/or may be positioned simultaneously while holding the patient and the IV needle (not requiring a third hand or an external mounting device).

In certain variations the imaging, system or device allows the care giver to hold the device and the patient simultaneously with the same hand, freeing the second hand to hold and manipulate the IV needle. The device may provide an in-plane display of the needle and vein near the point of needle insertion so the caregiver can view both simultaneously. The device may show a magnified view of the insertion point to permit correct needle vein alignment. The device may include a survey mode that allows the care-giver to rapidly scan a large area to find the best location for IV insertion. The device may estimate the size of the vein to allow the care-giver to select the patient's proper needle size. The device may provide ways to increase vein contrast allowing deeper veins to be imaged.

In certain variations, a vein visualization device that mounts or attaches on the IV inserter's hand, finger, or thumb ma include an IR source, a video sensor or camera, and visualization display that shows the location of the veins underneath the skin, where such mounting or attaching does not interfere with standard needle insertion methodology or normal needle insertion or hand use. Indeed, one hand can hold the IV needle for insertion and the other hand or a device protuberance can press on the vein, while providing an unobstructed view of the needle entry point. The visualization device may include an external display mounted in such a fashion that both the image and the insertion point are simultaneously within the IV inserter's field-of-view. The external display is adjacent to the area of veins and is parallel to the plane of the skin and approximately in-plane to the skin area containing the veins being, examined for IV insertion. The external display may be positioned behind and close to the area that is being examined for IV insertion and may be at an angle to the plane of the skin to facilitate viewing.

The video camera may be mounted with the display by using a mirror to redirect the reflection from the epidermis to the camera lens, on a stalk with the lens directly pointing to the skin, or on the electronics module directly pointing to the skin. Regardless of the placement/location of the camera there the device may include a mechanism to manually adjust the camera's light path to modify the location of the image while holding the device in one place.

The visualization device proactively enables registration between the vein image and the skin area being examined and determines image orientation, e.g., by including the device or a hand or thumb in the image. For example, at least part of the vein viewing device may be included in the image such as the edge of the display holder. The edge may include scale marks which are visible on the display as well as on the device and provide a visual reference to register the display to the skin location and thus to the veins.

Alternatively, the device can project a visible and co-located infrared light which can be seen on the display as well as on the skin providing registration between the two. A portion of the visualization means may show the complete field of view of the camera and a second portion of the visualization means may show a magnified image of a portion of the field-of-view. The magnification may be set manually by the user using button(s), thumb wheel, or touch mechanism. The magnification may be set automatically based upon the width of the needle. The amount of magnification may be displayed in the visualization. The location of the magnified image may be located anywhere in the visualization or fixed in a portion of the visualization subject to the constraint that it is within the field-of-view of the person carrying out the IV insertion. The device may be carried around in a pocket or clipped to clothing.

The system or device may include an indicator that provides information on the alignment and centering of the needle with respect to the blood vessel. The indicator may be in the form of an indication or signal on the display or a projection onto the skin. For example, a laser, DLP or LED may be projected and appear visibly on the patient's skin to signal proper alignment between a needle and blood vessel.

In certain variations, the imaging system or device may include any of the following features: an angled optical path to minimize specular reflection; separation of an optical path of an illumination source from a detector to minimize specular reflection; and/or camera gamma correction to optimize dynamic range at the patient's skin light level. The device may provide or include: as display of the IV or blood draw needle when specular light is reflected back to the camera or of the needle's shadow when specular light is reflected away from the camera; Initial magnification in survey mode to provide the camera's complete field-of-view on the display; Increased magnification of an insertion site during insertion mode; Magnification during insertion mode initially based upon vein or needle width; Restriction of the image or view to the area around needle tip during insertion mode; Software that automatically handles magnification but magnification may still be manually adjusted by the caregiver; Determination of vein width knowing the magnification; Canting of the lens to sensor to correct the aspect ratio if the angle of the sensor is non-perpendicular to the patient's skin; and/or Processor correction of the image to correct for the aspect ratio if the angle of the sensor is non-perpendicular to the patient's skin. Alternatively, the device may in include: a clam shell; Thumb-wheel for making magnification adjustment; and/or a removable base for cleaning, to accommodate different caregiver hand sizes, and to accommodate different attachment or holding methods.

A device or system may include or provide the following features: allow for a visual of both the actual insertion site and a virtual image without moving the caregiver's eye; an unobstructed view of needle entry point; No change in needle insertion methodology during use of the imaging system or device; two hands can hold the device, patient, and needle; and/or the display may provide image rotation to match user's perspective.

Any of the imaging systems or devices described herein may include one or more of the following features.

An imaging system or device my use false color, such as blue, to highlight blood vessel locations.

An imaging system may include a laser or LED pointer projection system that appears visibly on the skin and/or also on the display to determine where the image sensor or camera of the imaging system is pointing and where the blood vessel is positioned on the patient's anatomy.

The imaging system may project a visible and co-located infrared light which can be seen on the display as well as on the skin providing, registration between the two.

Part of the imaging system, such as an edge, may be included in the image, where the edge may include scale marks which are visible in the image on the display as well as on the system, next to the patient's skin, and provide a visual reference to register the display to the skin location and thus to the blood vessels. A scale may appear both in the image and also next to the patients skin, to show both location and magnification of a blood vessel.

A digital light projector, e.g., the Texas Instruments DLP Pico Display may be used to overlay a blood, vessel image on the body. The DLP may be used to overlay vein placement on the body and/or information as to the alignment between the vein and needle, e.g., by projecting side bars, arrows, suggested needle placement, etc.

Alternatively, a laser or LED beam may be modulated onto the skin, where the LED would be off if the needle were not near the blood vessel, would blink slowly if near but not on, and blink fast as the needle alignment and position got better until the was continuously on.

One of the problems with IV insertion occurs in older patients where a vein wanders when the needle is being, inserted. It can be very frustrating (and painful) when the vein is clearly seen but the needle is missing the target. This occurs due to inadequate connective tissue to hold the vein in a fixed position. An edge of the imaging system or device combined with the pressure applied, by the caregiver's thumb may be sufficient to hold the vein steady during IV insertion.

The imaging system may be small and inexpensive enough to be included, e.g., in a nurse or other caregiver's IV kit. The imaging system would be readily available and it would be the responsibility of the user to ensure its location and safety. The time waste associated with trying to track down an imaging system would be eliminated or reduced. The imaging system will function and can be attached to the caregiver when the caregiver is wearing gloves (which are required by hospital rules).

The imaging system may use a single button to cycle through various magnifications to increase magnification by a known amount, which is especially useful in pediatric cases where both the blood vessels and needle are small.

The imaging system may be able to magnify the horizontal scale only, if desired, to allow accurate needle placement while leaving the vertical scale unmagnified to provide for a better range of needle length. This is helpful where bigger diameter needles which are also longer are used. Such needles have an insertion point that is further from the thumb which holds the vein and over which the needle crosses.

Having mechanisms that allow for accurate magnification lakes it easier to size a needle. Larger veins allow larger needles for taster infusion, and accurate magnification can ensure that the optimal needle size is used.

The imaging system may include an inexpensive, throwaway cover to prevent contamination. The system may be constructed in a manner that makes wipe down easy for sterilization. The base of the system or unit may be removed in case of blood contamination and the device may have different bases to accommodate different hand sizes.

Hand mounted imaging devices as described herein don't suffer from the drawbacks of head mounted imaging devices. Indeed, people are used to moving their hands to touch a specific point on an object. When the user is holding the arm and vein of a patient prior to inserting an IV, the magnification is fixed, and the location of the vein is known by the match up between the display image of the scale and the real scale. Normal depth perception is present, and the device is unlikely to be moving since it is held by the thumb holding the vein and potentially resting on the patient's skin, leading, to a steady image. Also, the ability to quickly wipe the unit with alcohol or disinfectant minimizes the chance of unwanted infection that occurs when moving a head-mounted device from person to person.

The imaging systems and devices described herein allow a user to view the image and actual area being examined without causing mental fatigue or headaches. As the image and actual site are next to each other, moving the caregiver's head to find the best vein would not change the two viewed positions and their magnifications differently. The virtual and real views can be viewed without losing depth vision. The device works the same for users wearing glasses.

When inserting an IV, head placement is not constrained by the line of sight requirements and hand position that constrains head mounted devices. This allows the user to avoid neck and back strain. A user can move their head to attend to other issues without having to repeat the identification of a proper head location. Further aids are not required for exact magnification and position. Movement of the caregiver's head or movement by the patient won't change the apparent location of the vein. The device can by shared between users without the concern of transmitting an infection or lice.

Any of the variations of systems, device, and methods described herein may be combined with existing technology.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, of use of a "negative" limitation. Unless defined otherwise, all technical and scientific terms used herein have the same meaning, as commonly understood by one of ordinary skill in the art to which this invention belongs.

This disclosure is not intended, to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. An imaging system for aiding a needle insertion at a needle insertion site in a patient by a user, the imaging system comprising:
   a mountable unit comprising an illumination source, an image sensor, and a display for displaying an image based on image information from the image sensor;
   wherein the mountable unit further includes an attachment member permitting the user to mount the mountable unit to a hand of the user such that the hand of the remains free to hold the patient during needle insertion by the user while the mountable unit remains stationary where the attachment member is positioned such that a portion of the mountable unit can be rested on the hand of the user or on a skin of the patient; and
   wherein the display is attached to the mountable unit such that when the display produces an image of a blood vessel and the needle, the display can be positioned next to the needle insertion site when the user is holding the patient with the hand on which the mountable unit is attached such that the needle insertion site and the image of the blood vessel and needle are simultaneously within the user's field of view during needle insertion by the user.

2. The system of claim 1, wherein the mountable unit remains stationary during needle insertion as the user's hand on which the unit is attached holds the patient.

3. The system of claim 2, wherein the mountable unit remains stationary during needle insertion and does not add mass to the needle insertion motion which would impact the ability to properly insert the needle.

4. The system of claim 1, wherein the view of the needle insertion site is in its natural state, unobstructed by a projection or projected image.

5. The system of claim 1, wherein the display is attached to the mountable unit such that the display is positioned in substantially the same plane as the needle insertion site; or the display is attached to the mountable unit such that the display is positioned side by side with the needle insertion site; or the display is attached to the mountable unit such that the display is positioned at an angle to the plane of the needle insertion site.

6. The system of claim 1, wherein at least one of at least a portion of the mountable unit and at least a portion of the hand on which the unit is mounted is present in the image on the display to provide a reference point for the blood vessel location.

7. The system of claim 1, wherein a portion of the mountable unit includes a scale, wherein the scale appears in the image and next to the patient's skin to show location and/or magnification of a blood vessel.

8. The system of claim 1, wherein the mountable unit includes a strap, movable locking slide, or clamp for attachment to a hand, thumb, finger, wrist, or arm.

9. The system of claim 1, wherein the image sensor and/or illumination source are positioned at an angle to the patient's skin such that specular reflection from the skin surface is reflected away from the image sensor to minimize degradation of image quality.

10. The system of claim 1, wherein the display is configured to increase or decrease a magnification of the needle insertion site and the image of the blood vessel.

11. The system of claim 10, wherein the display is configured to display a degree of magnification; or where the display automatically selects the magnification of the image based upon the width, in pixels, of the needle.

12. The system of claim 1, further comprising a processor configured to add false color to the image to highlight blood vessel locations.

13. The system of claim 1, further comprising an indicator that provides information on the alignment and centering of the needle with respect to the blood vessel.

14. The system of claim 13, wherein the indicator comprises at least one of an indication which appears on the display and a projection which is projected onto the patient's skin.

15. The system of claim 14, wherein a laser, DLP or LED is projected and appears visibly on the patient's skin to signal proper alignment between a needle and blood vessel.

16. The system of claim 1, wherein the mountable unit further comprises a filter for filtering reflected light.

* * * * *